United States Patent
Rogers et al.

(10) Patent No.: US 7,130,396 B2
(45) Date of Patent: *Oct. 31, 2006

(54) MEDICAL MONITORING SYSTEM HAVING MULTIPLE COMMUNICATIONS CHANNELS

(75) Inventors: Bobby E. Rogers, San Diego, CA (US); William R. Marable, Gurnee, IL (US); Philip N. Eggers, Poway, CA (US)

(73) Assignee: CardioNet, Inc., San Diego, CA (US)

( * ) Notice: Subject to any disclaimer, the term of this patent is extended or adjusted under 35 U.S.C. 154(b) by 181 days.

This patent is subject to a terminal disclaimer.

(21) Appl. No.: 10/737,193

(22) Filed: Dec. 15, 2003

(65) Prior Publication Data

US 2004/0146149 A1    Jul. 29, 2004

Related U.S. Application Data

(63) Continuation-in-part of application No. 09/841,133, filed on Apr. 23, 2001, now Pat. No. 6,665,385.

(51) Int. Cl.
   *H04M 11/00* (2006.01)

(52) U.S. Cl. .............................. 379/106.02; 379/93.08; 128/903; 128/904

(58) Field of Classification Search ........... 379/106.02, 379/106.01, 90.01, 93.05–93.08, 93.28, 37, 379/38; 128/903, 904; 340/10.41, 573.4
See application file for complete search history.

(56) References Cited

U.S. PATENT DOCUMENTS

| | | | |
|---|---|---|---|
| 3,478,344 A | 11/1969 | Schwitzgebel et al. ..... 340/312 |
| 3,768,014 A | 10/1973 | Smith et al. ............ 324/158 R |
| 3,885,552 A | 5/1975 | Kennedy ............... 128/2.05 R |
| 3,902,478 A | 9/1975 | Konopasek et al. .... 128/2.06 F |
| 3,925,762 A | 12/1975 | Keitlinger et al. .......... 340/150 |
| 4,173,971 A | 11/1979 | Karz ........................... 128/702 |
| 4,183,354 A | 1/1980 | Sibley et al. ................ 128/711 |
| 4,211,237 A | 7/1980 | Nagel .......................... 128/698 |
| 4,230,127 A | 10/1980 | Larson ........................ 128/706 |
| 4,241,237 A | 12/1980 | Paraskevakos et al. .. 179/2 AM |
| 4,457,315 A | 7/1984 | Bennish ....................... 128/704 |
| 4,531,527 A | 7/1985 | Reinhold, Jr. et al. ...... 128/696 |
| 4,535,783 A | 8/1985 | Marangoni .................. 128/711 |
| 4,598,272 A | 7/1986 | Cox ............................ 340/539 |
| 4,651,157 A | 3/1987 | Gray et al. ................. 342/457 |
| 4,675,656 A | 6/1987 | Narcisse ...................... 340/539 |
| 4,706,689 A | 11/1987 | Man ............................ 128/903 |
| 4,742,357 A | 5/1988 | Rackley ...................... 342/457 |

(Continued)

FOREIGN PATENT DOCUMENTS

DE      4414 907      6/1995

(Continued)

*Primary Examiner*—Stella woo
(74) *Attorney, Agent, or Firm*—Fish & Richardson P.C.

(57) ABSTRACT

A medical monitoring system has a sensor system including a sensor associated with a patient and a remote monitoring unit. The remote monitoring unit includes a microprocessor in communication with the sensor system, and a portable-monitoring unit transceiver system in communication with the microprocessor. The portable-monitoring unit transceiver system has a land-line telephone transceiver and/or a cellular telephone transceiver, and a third-network transceiver such as a paging-network transceiver. A full data set is transmitted over the land-line telephone transceiver or the cellular telephone transceiver when communications links over these transceivers are available, and a reduced data set is transmitted over the third-network transceiver when communications links over the land-line telephone transceiver and the cellular telephone transceiver are not available.

17 Claims, 1 Drawing Sheet

U.S. PATENT DOCUMENTS

| | | | |
|---|---|---|---|
| 4,750,197 A | 6/1988 | Denekamp et al. ............ 379/58 |
| 4,777,478 A | 10/1988 | Hirsch et al. ................ 340/573 |
| 4,785,291 A | 11/1988 | Hawthorne ................ 340/573 |
| 4,819,860 A | 4/1989 | Hargrove et al. ........... 228/668 |
| 4,952,928 A | 8/1990 | Carroll et al. |
| 5,003,984 A | 4/1991 | Muraki et al. ............... 128/710 |
| 5,113,869 A | 5/1992 | Nappholz et al. ........... 128/696 |
| 5,172,698 A | 12/1992 | Stanko ........................ 128/697 |
| 5,223,844 A | 6/1993 | Mansell et al. .............. 342/357 |
| 5,301,105 A | 4/1994 | Cummings, Jr. ............. 364/401 |
| 5,309,920 A | 5/1994 | Gallant et al. ............... 128/710 |
| 5,311,197 A | 5/1994 | Sorden et al. ............... 342/457 |
| 5,318,592 A | 6/1994 | Schaldach ...................... 607/5 |
| 5,321,618 A | 6/1994 | Gessman ................. 364/413.06 |
| 5,334,974 A | 8/1994 | Simms et al. ................ 340/990 |
| 5,335,664 A | 8/1994 | Nagashima ................. 128/696 |
| 5,336,245 A | 8/1994 | Adams ......................... 607/32 |
| 5,348,008 A | 9/1994 | Bornn et al. ................. 128/642 |
| 5,389,934 A | 2/1995 | Kass ............................ 342/357 |
| 5,394,879 A | 3/1995 | Gorman ....................... 128/707 |
| 5,418,537 A | 5/1995 | Bird ............................ 342/356 |
| 5,422,816 A | 6/1995 | Sprague et al. ............. 364/449 |
| 5,423,869 A | 6/1995 | Poore ........................... 607/18 |
| 5,458,123 A | 10/1995 | Unger ......................... 128/696 |
| 5,461,365 A | 10/1995 | Schlager et al. ............. 340/573 |
| 5,470,233 A | 11/1995 | Fruchterman et al. ....... 434/112 |
| 5,479,482 A | 12/1995 | Grimes ......................... 379/59 |
| 5,487,755 A | 1/1996 | Snell et al. .................... 607/27 |
| 5,497,149 A | 3/1996 | Fast ............................. 340/988 |
| 5,503,158 A | 4/1996 | Coppock et al. ............. 128/696 |
| 5,504,491 A | 4/1996 | Chapman .................... 342/357 |
| 5,515,419 A | 5/1996 | Sheffer ......................... 379/58 |
| 5,522,396 A | 6/1996 | Langer et al. ............... 128/696 |
| 5,544,661 A | 8/1996 | Davis et al. ................. 128/700 |
| 5,549,113 A | 8/1996 | Halleck et al. .............. 128/671 |
| 5,564,429 A | 10/1996 | Bornn et al. ................. 128/696 |
| 5,568,814 A | 10/1996 | Gallant et al. ............... 128/672 |
| 5,573,506 A | 11/1996 | Vasko .......................... 604/65 |
| 5,576,952 A | 11/1996 | Stutman et al. ......... 364/413.02 |
| 5,579,001 A | 11/1996 | Dempsey et al. |
| 5,579,775 A | 12/1996 | Dempsey et al. ............ 128/670 |
| 5,617,871 A | 4/1997 | Burrows ...................... 128/696 |
| 5,620,472 A | 4/1997 | Rahbari ........................ 607/27 |
| 5,626,624 A | 5/1997 | Schaldach et al. ............ 607/24 |
| 5,626,630 A | 5/1997 | Markowitz et al. ........... 607/60 |
| 5,629,678 A | 5/1997 | Gargano et al. ............. 340/573 |
| 5,634,468 A | 6/1997 | Platt et al. |
| 5,649,303 A | 7/1997 | Hess et al. .................... 455/63 |
| 5,652,570 A | 7/1997 | Lepkofker ................... 340/573 |
| 5,678,562 A | 10/1997 | Sellers ........................ 128/710 |
| 5,704,351 A | 1/1998 | Mortara et al. .............. 128/630 |
| 5,704,364 A | 1/1998 | Saltzstein et al. ........... 128/696 |
| 5,704,366 A | 1/1998 | Tacklind et al. ............. 128/716 |
| 5,713,856 A | 2/1998 | Eggers et al. ................. 604/65 |
| 5,720,770 A | 2/1998 | Nappholz et al. ............. 607/30 |
| 5,720,771 A | 2/1998 | Snell ............................. 607/60 |
| 5,724,025 A | 3/1998 | Tavori ........................ 340/573 |
| 5,729,197 A | 3/1998 | Cash ........................... 340/539 |
| 5,730,143 A | 3/1998 | Schwarzberg ............... 128/710 |
| 5,731,757 A | 3/1998 | Layson, Jr. ................. 340/573 |
| 5,748,103 A | 5/1998 | Flach et al. ............ 340/870.07 |
| 5,749,367 A | 5/1998 | Gamlyn et al. .............. 128/696 |
| 5,749,907 A | 5/1998 | Mann ........................... 607/27 |
| 5,752,976 A | 5/1998 | Duffin et al. .................. 607/32 |
| 5,759,199 A | 6/1998 | Snell et al. .................... 607/60 |
| 5,882,300 A | 3/1999 | Malinouskas et al. ....... 600/300 |
| 5,891,169 A | 4/1999 | Boheim et al. ................. 607/4 |
| 5,913,827 A | 6/1999 | Gorman ...................... 600/509 |
| 5,913,881 A | 6/1999 | Benz et al. .................... 607/36 |
| 5,931,791 A | 8/1999 | Saltzstein et al. ........... 600/513 |
| 5,941,829 A | 8/1999 | Saltzstein et al. ........... 600/509 |
| 5,944,659 A | 8/1999 | Flach et al. ................. 600/300 |
| 5,950,110 A | 9/1999 | Hendrickson .................. 455/1 |
| 5,959,529 A | 9/1999 | Kail, IV |
| 5,964,794 A | 10/1999 | Bolz et al. ................... 607/121 |
| 5,966,692 A | 10/1999 | Langer et al. |
| 5,970,986 A | 10/1999 | Bolz et al. ................... 128/899 |
| 5,987,352 A | 11/1999 | Klein et al. ................. 600/509 |
| 5,987,519 A | 11/1999 | Peifer et al. ................. 709/230 |
| 6,026,008 A | 2/2000 | Feese ........................... 365/63 |
| 6,038,469 A | 3/2000 | Karlsson et al. ............ 600/512 |
| 6,073,046 A | 6/2000 | Patel et al. .................. 600/509 |
| 6,083,248 A | 7/2000 | Thompson .................... 607/30 |
| 6,088,608 A | 7/2000 | Schulman et al. .......... 600/345 |
| 6,093,146 A | 7/2000 | Filangeri .................... 600/300 |
| 6,101,478 A | 8/2000 | Brown ........................... 705/2 |
| 6,102,856 A | 8/2000 | Groff et al. ................. 600/301 |
| 6,122,514 A * | 9/2000 | Spaur et al. |
| 6,154,674 A | 11/2000 | Meier ........................... 607/23 |
| 6,160,478 A | 12/2000 | Jacobsen et al. ............ 340/539 |
| 6,181,966 B1 | 1/2001 | Nigram ........................... 607/4 |
| 6,192,274 B1 | 2/2001 | Worzewski .................... 607/14 |
| 6,225,901 B1 | 5/2001 | Kail, IV ...................... 340/539 |
| 6,245,092 B1 | 6/2001 | Schaldach ...................... 607/1 |
| 6,263,243 B1 | 7/2001 | Lang ............................ 607/17 |
| 6,287,252 B1 | 9/2001 | Lugo |
| 6,466,793 B1 | 10/2002 | Wallstedt et al. ........... 455/450 |
| 6,665,385 B1 * | 12/2003 | Rogers et al. ......... 379/106.02 |
| 2002/0143576 A1 | 10/2002 | Nolvak et al. |

FOREIGN PATENT DOCUMENTS

| | | |
|---|---|---|
| EP | 0 484 880 | 11/1991 |
| EP | 0 834 846 | 1/1996 |
| EP | 0 811 959 | 6/1997 |
| EP | 1 072 994 | 1/2001 |
| FR | 2 787 905 | 12/1998 |
| JP | 06-502270 | 3/1994 |
| JP | 08-243131 | 9/1996 |
| WO | WO 94/13197 | 6/1994 |
| WO | WO 96/25877 | 8/1996 |
| WO | WO 97/00708 | 1/1997 |
| WO | WO 99/44494 | 9/1999 |
| WO | WO 99/56613 | 11/1999 |
| WO | WO 00/30529 | 6/2000 |
| WO | WO 00/62663 | 10/2000 |

* cited by examiner

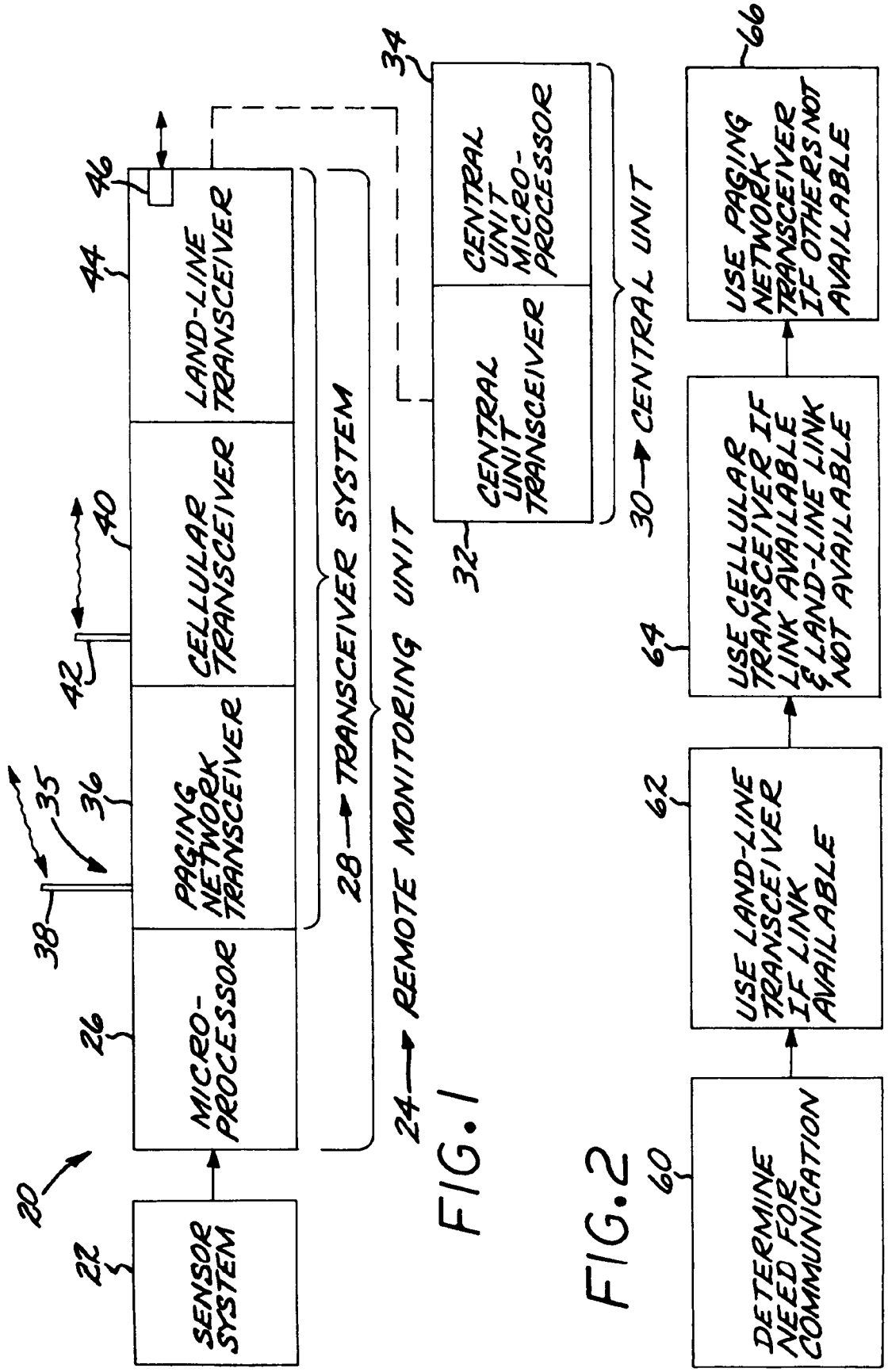

MEDICAL MONITORING SYSTEM HAVING MULTIPLE COMMUNICATIONS CHANNELS

CROSS-REFERENCE TO RELATED APPLICATION

This application is a continuation-in-part application of, and claims priority under 35 U.S.C. 120 to, U.S. application Ser. No. 09/841,133, filed Apr. 23, 2001, which issued on Dec. 16, 2003 as U.S. Pat. No. 6,665,385, the disclosure of which is incorporated by reference.

BACKGROUND

The following description relates to a medical monitoring system having multiple communications channels, e.g., for providing alternative information pathways between a medical monitoring unit and a central monitoring station.

Advances in sensor technology, electronics, and communications have made it possible for physiological characteristics of patients to be monitored even when the patients are ambulatory and not in continuous, direct contact with a hospital monitoring system. For example, U.S. Pat. No. 5,959,529 describes a monitoring system in which the patient carries a remote monitoring unit with associated physiological sensors. The remote monitoring unit conducts a continuous monitoring of one or more physiological characteristics of the patient, such as the patient's heartbeat and its waveform, according to a medical condition of the patient.

An objective of such portable monitoring systems is to establish contact with a central; monitoring station (a.k.a., a central unit), which is in turn may contact with medical personnel and/or access the patient's medical records. The ability to establish contact allows the central unit to determine the existence of a medical emergency with the patient, and to render medical assistance to the patient during such an emergency. The ability to establish contact is also important psychologically to the patient, so that the patient knows that (s)he is not alone or out of touch. The portable monitoring systems may establish one or more communication links to the central unit through telephone land-lines, when the patient is in a location where land-line telephone access is readily available or through the cellular telephone system when land-line access is not available or an emergency suddenly occurs.

SUMMARY

The present inventors recognized that existing medical monitoring systems may be hampered by the fact that cellular telephone communication links are not available in many parts of the United States and in other countries. This unavailability arises because the cellular system infrastructure is not in place in relatively remote areas and because cellular telephone signals will not penetrate into many structures even if they are within the range of cellular telephone transceiver cell sites. As a result, the remote monitoring unit is unable to communicate with the central unit from many locations. The patient is therefore unable to obtain emergency assistance in those locations, and consequently feels isolated. Accordingly, the inventors developed various systems and techniques that help ensure wide-area communication availability for remote monitoring units of medical monitoring systems.

The systems and techniques disclosed here may include various combinations of the following features.

In one aspect, a medical monitoring system includes a sensor unit configured to sense one or more physiological characteristics of a patient, a monitoring unit in communication with the sensor unit and operable to communicate information relating to the sensed physiological characteristics to a central unit, and two or more communications channels operable to communicate between the monitoring unit and the central unit. The monitoring unit is operable to specify for transmission a data set that is tailored to a particular communications channel to be used to communicate the information relating to the sensed physiological characteristics to the central unit.

The tailored data set for transmission my be a subset of a full data set or may be information derived from a data set. More generally, the tailored data set may include a data set that is adapted according to one or more parameters of the selected communications channel.

The monitoring unit may further be operable to select a communications channel from among the two or more communications channel, for example, based on one or more predetermined criteria such the communications channels' relative availability, bandwidth, quality, latency, cost, reliability, and the like. The communications channels may include one or both of wired and wireless communications channels and, further, may include one or more of a land-line telephone network, a cellular telephone network, a paging network and a packet-switched data network.

In another aspect, a portable medical monitoring unit may be controlled by receiving sensor data from a sensor, the received sensor data representative of one or more physiological characteristics of a patient being monitored, selecting a communications channel from among multiple potential communications channels, specifying a data set for transmission to a central unit, the specified data set being adapted to the selected communications channel, and transmitting the specified data set over the selected communications channel to the central unit.

Selecting the communications channel from among the potential communications channels may be based on one or more predetermined criteria such as the communications channels' relative availability, bandwidth, quality, latency, cost and reliability.

Specifying the data set for transmission to the central unit may include adapting the data set according to one or more parameters of the selected communications channel. The specified data set for transmission may include a subset of a full data set or may be information derived from a data set.

The systems and techniques described here may provide one or more of the following advantages. For example, a medical monitoring system having a remote monitoring unit may provide enhanced communications coverage throughout the United States and/or much of the world. This communications coverage may include a wide geographical area and/or locations such as the interiors of buildings that are sometimes unavailable for cellular telephone coverage. This enhanced communications coverage increases the likelihood that the remote monitoring unit will be able to communicate with the central unit under emergency conditions. Equally importantly, the patient being monitored has better peace of mind of knowing that (s)he is rarely, if ever, out of touch with medical assistance. The present approach may be implemented relatively inexpensively, as it can rely on communications infrastructure that already is in place and operating, and it may be adapted to new communications technologies that become available. The remote monitoring unit can be made to work with this approach with little, if any, increase in size, weight, and/or power consumption to the remote monitoring unit.

Other features and advantages will be apparent from the following description taken in conjunction with the accompanying drawings and the claims.

DRAWING DESCRIPTIONS

FIG. 1 is a schematic diagram of a medical monitoring system; and

FIG. 2 is a block flow diagram of a method of operating the multiple communication channels.

DETAILED DESCRIPTION

FIG. 1 depicts a medical monitoring system 20 that includes a sensor system 22 having a sensor for monitoring any of a variety of physiological characteristics associated with a patient, for example, a heartbeat waveform, blood pressure, brain signals, blood chemistry, and the like. The sensor system 22 communicates with a remote monitoring unit (RMU) 24 that typically is either carried by the patient or is relatively physically close to the patient. The communication between the sensor system 22 and the remote monitoring unit 24 may be either wired or wireless, such as a short-range radio frequency link.

The remote monitoring unit 24 includes a microprocessor 26 in communication with the sensor system 22. The microprocessor 26 performs computations as may be necessary and oversees the operation of a portable-monitoring unit transceiver system 28 that is also a part of the remote monitoring unit 24. The portable-monitoring-unit transceiver system 28 communicates with a central unit (CU) 30 having a central-unit transceiver system 32 that supports communications of the types found in the portable-monitoring-unit transceiver system 28 and which will be discussed subsequently. The central unit 30 also includes a central unit microprocessor 34 that coordinates the central-unit transceiver system 32 and performs other analytical and control functions. The general features of a preferred form of the medical monitoring system 20, other than those to be discussed subsequently, are described in U.S. Pat. No. 5,959,529, whose disclosure is incorporated by reference.

The portable-monitoring-unit transceiver system 28 includes a third-network transceiver 35. The third-network transceiver 35 may be a two-way paging-network transceiver operable with the paging network. However, the third-network transceiver 35 may be of other types, such as a specialized emergency-network transceiver, a marine-network transceiver, and the like. Alternatively, or in addition, the third-network transceiver 35 may be configured to establish a communication link by other available means, among others, such as wired or wireless networks that implement communications protocols and standards such IP (Internet protocol), WiFi (IEEE 802.11x), WiMax (IEEE 802.16x), and/or GPRS (General Packet Radio Service). Moreover, the third network transceiver may be configured to communicate over either circuit-switched networks (e.g., traditional telephone networks) or over packet-switched data networks.

The example implementation shown in FIG. 1 includes the paging network transceiver 36 and its antenna 38 that selectively establish a third-network link (in this case a paging network link) with the central unit 30. The paging network transceiver 36 operates using the existing paging network available throughout the United States and much of the rest of the world. Communication with the paging network is available in virtually every part of the United States and in most parts of the rest of the world. It is available in the open, inside buildings, in aircraft, and onboard ships. The paging network originally operated unidirectionally with signals conveyed only from the satellite to the paging unit, but it is now available in a bidirectional form as suggested by the term "transceiver", an art-recognized contraction of "transmitter/receiver". That is, the bidirectional paging transceiver 36 may either receive information or send information, via the existing paging system, to the central unit transceiver 32.

The portable-monitoring-unit transceiver system 28 further includes a cellular telephone transceiver 40 and its antenna 42, which may serve as a primary wireless network transceiver. The cellular transceiver 40 selectively establishes a cellular link with the central unit 30. The cellular telephone transceiver 36 operates using the existing network of cell sites available through much of the United States and some of the rest of the world. Cellular communications links are operable in the open, inside most automobiles within range of cell sites, and inside many buildings, but are often not available in some buildings, in aircraft, or onboard ships. The cellular telephone transceiver 40 may either receive information or send information through the cellular network to the central unit transceiver 32.

The portable-monitoring-unit transceiver system 28 further includes a land-line telephone transceiver 44 and its plug jack 46. The land-line telephone transceiver 44 selectively establishes a land-line link with the central unit 30. The land-line telephone transceiver 44 operates using the land-line system (which may also include microwave links of the land-lines and/or may provide one or more of POTS (Plain Old Telephone Service), DSL (Digital Subscriber Line) or ISDN (Integrated Services Digital Network) service) available through much of the United States and much of the rest of the world. Land-line telephone communications links are available through telephone central switching offices wherever there is a plug connection, but the need for physical access to a plug tends to limit the mobility of the patient. The land-line telephone transceiver 44 may either receive information or send information through the land-line system to the central unit transceiver 32.

FIG. 2 depicts a sequence of events that may occur when communication is required between the remote monitoring unit 24 and the central unit 30. A need for communications is first determined (sub-process 60). This sub-process typically occurs when the remote monitoring unit 24 determines that it needs to communicate with the central unit 30, but it may also occur when the central unit 30 determines that it needs to communicate with the remote monitoring unit 24. The former case will be discussed in detail, but the discussion is equally applicable to the latter case.

The land-line transceiver 44 is used if the land-line link is available (sub-process 62). That is, the microprocessor 26 seeks to open a land-line communication link to the central unit 30 through the land-line transceiver 44. If there is no plug in the plug jack 46 or if it is otherwise not possible or feasible to dial up the central unit 30, then the microprocessor 26 seeks to open a cellular link to the central unit 30 through the cellular telephone transceiver 40 (sub-process 64). The use of the land-line transceiver 44 typically is preferred to the use of the cellular telephone transceiver 40, because the land-line communication link tends to be more reliable, more secure, and usually less costly, if available.

If the communication link is established either through the land-line transceiver 44 or the cellular transceiver 40, then the microprocessor 26 uses a first processing routine stored therein that transmits a full data set through either of these wide-bandwidth communications channels. This is the desired operating mode of the medical monitoring system 20, because its full data capabilities may be employed.

However, as noted above, in some instances neither the land-line link nor the cellular link is available due to reasons such as unavailability of the land line, unavailability of the cellular system, user overload of the cellular system, interference to wireless communications in the frequency band of the cellular system, or the like. In that case, the third-network transceiver 36 is used (sub-process 66) to employ an alternative communications channel such as the paging network or an available wired or wireless packet-switched network, such as the Internet. If the third-network provides a reduced communications bandwidth, e.g., in comparison the cellular or land-lines networks, then the microprocessor 26 may use a second processing routine stored therein that determines and transmits a reduced data set over the paging-network link. In some cases where the sensor system 22 obtains a small amount of data such as a single blood chemistry number, the full data set may be transmitted over the paging network transceiver 36. In other cases where the sensor system 22 obtains much larger amounts of data, such as a heartbeat waveform, then it may not be possible or feasible (e.g., due to network latency or other delays) to transmit the full data set even if data compression techniques are used. The second processing routine is written to select some subset of the data (e.g., the most important) that is gathered by the sensor system 22, and/or to calculate or otherwise generate secondary data from the gathered data (e.g., data derived from, and representative of, the sensed data), for transmission over the paging network transceiver 36. In the case of the heartbeat, for example, the second processing routine may calculate a heart rate (number of beats per minute), amplitude, and waveform characteristics of selected portions of the full heartbeat signal for transmission within the bandwidth constraints of the third-network. The second processing routine would typically not select voice or other audio signals for transmission. This reduced data set, while not as complete as the full data set, is far better and more useful to the central unit 30 in diagnosing and aiding the patient than having no information and no contact at all.

It is possible to perform multiple serial communications between the remote monitoring unit 24 and the central unit 30 to transmit more information, but even in that case it is unlikely that the full data set can be conveyed. The selection of the content of the reduced data set, and thus the content of the second processing routine, is left to the individual situation and type of data being monitored for the individual patient.

More generally, the transceiver system 28 of the remote monitoring unit 24 may employ multiple (i.e., two, three, four or more) different communications channels for communicating information from the remote monitoring unit 24 to the central unit 30. The microprocessor 26 then can rely on predetermined criteria (e.g., such as described in a table, database or software instructions) to select (and/or otherwise specifying or generating) a data set for transmission that is tailored to, or otherwise appropriate for, the particular communications channel being used. The predetermined criteria may be set or altered by a system designer or administrator, or even by a software process automatically, depending on several different factors including the types of physiological characteristics being monitored, the severity of the patient's condition, the available bandwidth, quality, latency, cost and/or reliability of the communications channel to be used, and the like.

The system described above may provide a communications hierarchy based upon a recognition that limited communications is better than no communications in many instances, and a recognition of the tradeoff between factors such as communications availability and bandwidth. Some currently available communications links are summarized in the following table, with the land-line telephone being a wired connection and the other communications links being wireless. However, it is emphasized that the use of the systems and techniques described here is not limited to these types of communications links and includes other presently available and future communications links:

| Communications Link | Center Frequency (MHZ) | Bandwidth (Qualitative) |
| --- | --- | --- |
| Land-line telephone | — | very high |
| Analog cellular phone | 859 | moderate |
| Digital CDMA cellular phone | 800 | high |
| Digital PCS CDMA cellular phone | 1900 | high |
| Motorola Reflex paging | 900 | moderate |
| Celemetry paging | 859 | very low |

Thus, in the implementation described above the portable-monitoring-unit transceiver system of the medical monitoring system includes the land-line telephone transceiver and a digital cellular transceiver. However, when communication over these communications links is not available, one or more of the alternative, third-networks (e.g., the paging network) may be used as a backup. Even data communications over a low-bandwidth or moderate-bandwidth paging system is preferable to no communication in many situations.

Although a particular implementation been described in detail for purposes of illustration, various modifications and enhancements may be made, for example, by combining, rearranging or substituting different features or sub-processes for those disclosed above. Accordingly, other embodiments are within the scope of the following claims.

What is claimed is:

1. A medical monitoring system comprising:
   a sensor unit configured to sense one or more physiological characteristics of a patient;
   a monitoring unit in communication with the sensor unit and operable to communicate information relating to the sensed physiological characteristics to a central unit; and
   a plurality of communications channels operable to communicate between the monitoring unit and the central unit, the monitoring unit operable to specify for transmission a data set that is tailored to a particular communications channel to be used to communicate the information relating to the sensed physiological characteristics to the central unit.

2. The system of claim 1 wherein the tailored data set for transmission comprises a subset of a full data set.

3. The system of claim 1 wherein the tailored data set for transmission comprises information derived from a data set.

4. The system of claim 1 wherein the monitoring unit is further operable to select a communications channel from among the plurality of communications channel.

5. The system of claim 4 wherein the monitoring unit selects the communication channel based on one or more predetermined criteria.

6. The system of claim 5 wherein the predetermined criteria include one or more of the communications channels' relative availability, bandwidth, quality, latency; cost and reliability.

7. The system of claim 4 wherein the tailored data set comprises a data set that is adapted according to one or more parameters of the selected communications channel.

8. The system of claim 1 wherein the plurality of communications channels include one or both of wired and wireless communications channels.

9. The system of claim 1 wherein the plurality of communications channels include one or more of a land-line telephone network, a cellular telephone network, a paging network and a packet-switched data network.

10. A method of controlling a portable medical monitoring unit, the method comprising:

receiving sensor data from a sensor, the received sensor data representative of one or more physiological characteristics of a patient being monitored;

selecting a communications channel from among a plurality of potential communications channels;

specifying a data set for transmission to a central unit, the specified data set being adapted to the selected communications channel; and transmitting the specified data set over the selected communications channel to the central unit.

11. The method of claim 10 wherein selecting the communications channel from among the plurality of potential communications channels is based on one or more predetermined criteria.

12. The method of claim 11 wherein the predetermined criteria include one or more of the communications channels' relative availability, bandwidth, quality, latency, cost and reliability.

13. The method of claim 10 wherein specifying the data set for transmission to the central unit comprises adapting the data set according to one or more parameters of the selected communications channel.

14. The method of claim 10 wherein the specified data set for transmission comprises a subset of a full data set.

15. The method of claim 10 wherein the specified data set for transmission comprises information derived from a data set.

16. The method of claim 10 wherein the plurality of communications channels include one or both of wired and wireless communications channels.

17. The method of claim 10 wherein the plurality of communications channels include one or more of a land-line telephone network a cellular telephone network, a paging network and a packet-switched data network.

* * * * *